United States Patent
Bomkamp et al.

(10) Patent No.: US 10,497,974 B2
(45) Date of Patent: Dec. 3, 2019

(54) FLUORINATED CARBONATES COMPRISING TWO OXYGEN BEARING FUNCTIONAL GROUPS

(71) Applicant: SOLVAY SA, Brussels (BE)

(72) Inventors: Martin Bomkamp, Hannover (DE); Dirk Seffer, Hannover (DE)

(73) Assignee: SOLVAY SA, Brussels (BE)

( * ) Notice: Subject to any disclaimer, the term of this patent is extended or adjusted under 35 U.S.C. 154(b) by 263 days.

(21) Appl. No.: 15/329,388

(22) PCT Filed: Jul. 29, 2015

(86) PCT No.: PCT/EP2015/067408
§ 371 (c)(1),
(2) Date: Jan. 26, 2017

(87) PCT Pub. No.: WO2016/016319
PCT Pub. Date: Feb. 4, 2016

(65) Prior Publication Data
US 2017/0214088 A1    Jul. 27, 2017

(30) Foreign Application Priority Data
Jul. 29, 2014  (EP) .................................... 14178916

(51) Int. Cl.
| | |
|---|---|
| *H01M 4/02* | (2006.01) |
| *H01M 10/0567* | (2010.01) |
| *C07C 69/96* | (2006.01) |
| *H01G 11/60* | (2013.01) |
| *B61L 3/00* | (2006.01) |
| *H01G 11/58* | (2013.01) |
| *H01M 10/0569* | (2010.01) |

(Continued)

(52) U.S. Cl.
CPC ......... *H01M 10/0567* (2013.01); *B61L 3/006* (2013.01); *B61L 3/008* (2013.01); *C07C 68/00* (2013.01); *C07C 69/96* (2013.01); *H01G 11/58* (2013.01); *H01G 11/60* (2013.01); *H01G 11/62* (2013.01); *H01G 11/64* (2013.01); *H01M 10/0525* (2013.01); *H01M 10/0569* (2013.01); *H01M 12/08* (2013.01); *H01M 10/052* (2013.01); *H01M 2300/0034* (2013.01); *Y02E 60/13* (2013.01)

(58) Field of Classification Search
CPC ....................................................... H01M 4/02
See application file for complete search history.

(56) References Cited

FOREIGN PATENT DOCUMENTS

| | | | |
|---|---|---|---|
| EP | 0 557 167 A1 | | 8/1993 |
| EP | 557-167 | * | 8/1993 |

(Continued)

OTHER PUBLICATIONS

Database CA [Online] Chemical Abstracts Service, Columbus, Ohio, US; 1997, Abe, Akihito et al: "Water- and oil-repelling cosmetics containing fluorinated silicones and acrylic acid polymers", XP002734050, retrieved from STN Database accession No. 1997:473603.

(Continued)

*Primary Examiner* — Jacob B Marks

(57) ABSTRACT

Fluorinated carbonates comprising two oxygen bearing functional groups, methods for the preparation thereof, and their use as solvent or solvent additive for lithium ion batteries and supercapacitors are disclosed.

5 Claims, 3 Drawing Sheets

LSV test of 3-electrode beaker cell with LiCoO₂ as a working electrode

(51) Int. Cl.
*C07C 68/00* (2006.01)
*H01G 11/62* (2013.01)
*H01G 11/64* (2013.01)
*H01M 10/0525* (2010.01)
*H01M 12/08* (2006.01)
H01M 10/052 (2010.01)

(56) References Cited

FOREIGN PATENT DOCUMENTS

| | | |
|---|---|---|
| JP | 9 143023 A | 6/1997 |
| JP | 2000-228216 A | 8/2000 |
| JP | 2000-327634 A | 11/2000 |
| JP | 2006-291008 A | 10/2006 |
| WO | 2011/006822 A1 | 1/2011 |
| WO | 2013/110741 A1 | 8/2013 |

OTHER PUBLICATIONS

Registry (STN) [online], Dec. 8, 2008 [retrieved Jan. 25, 2019] CAS Registration No. 1081814-32-5.

* cited by examiner

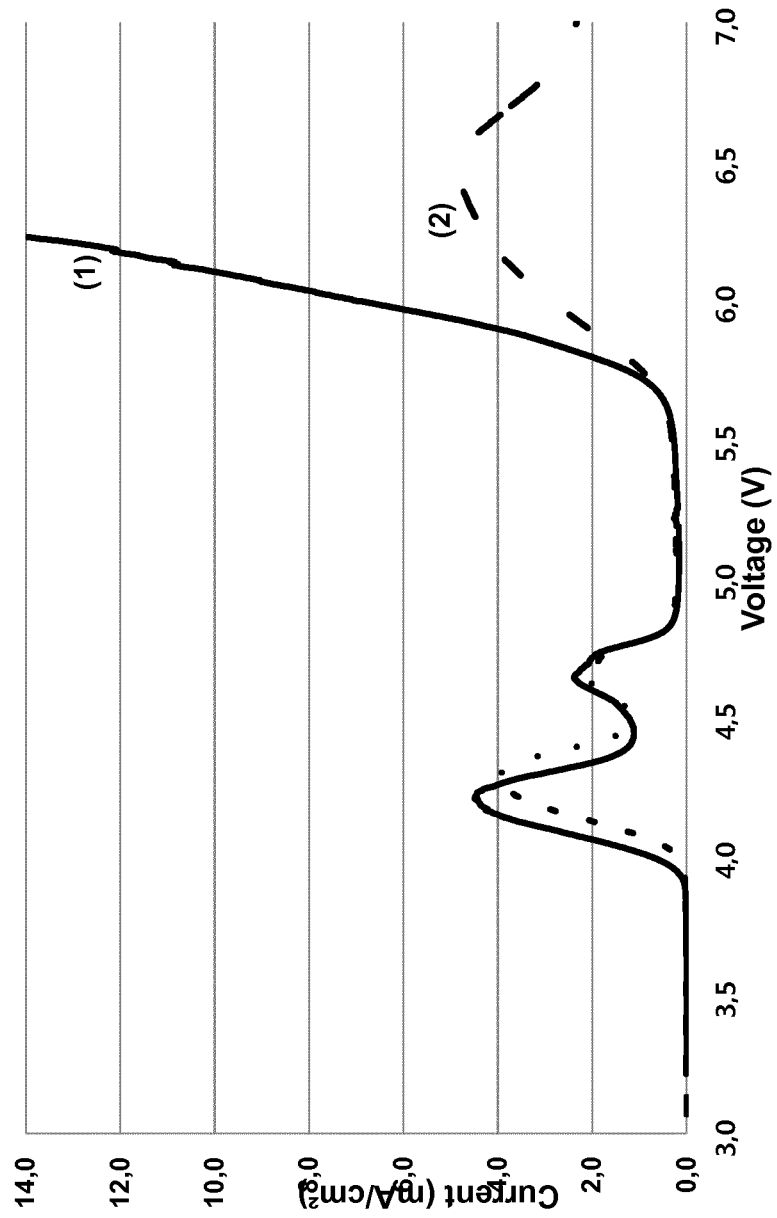
Figure 1. LSV test of 3-electrode beaker cell with $LiCoO_2$ as a working electrode

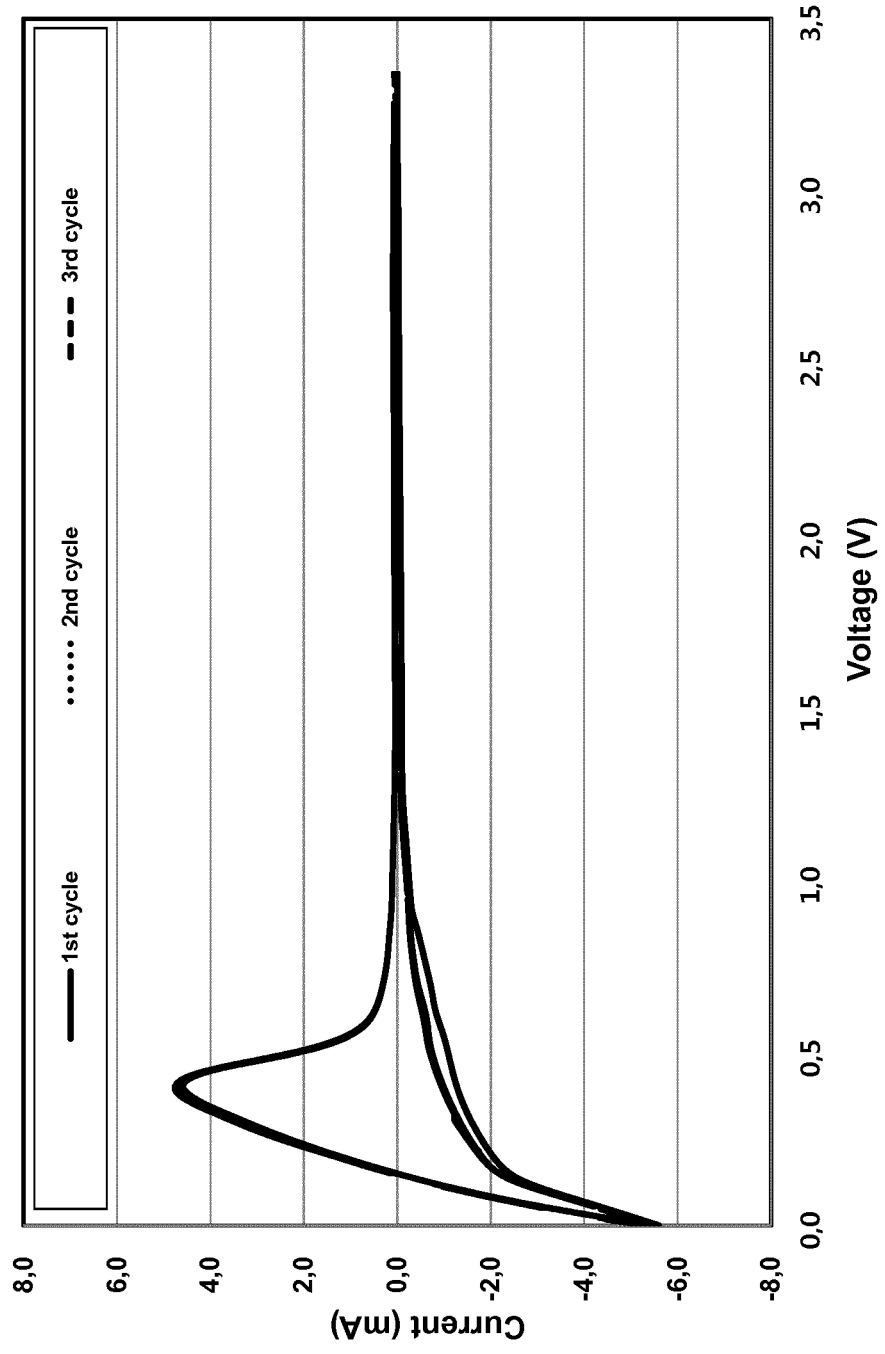
Figure 2. CV test of 3-electrode beaker cell with SCMG-AR (artificial graphite) as a working electrode

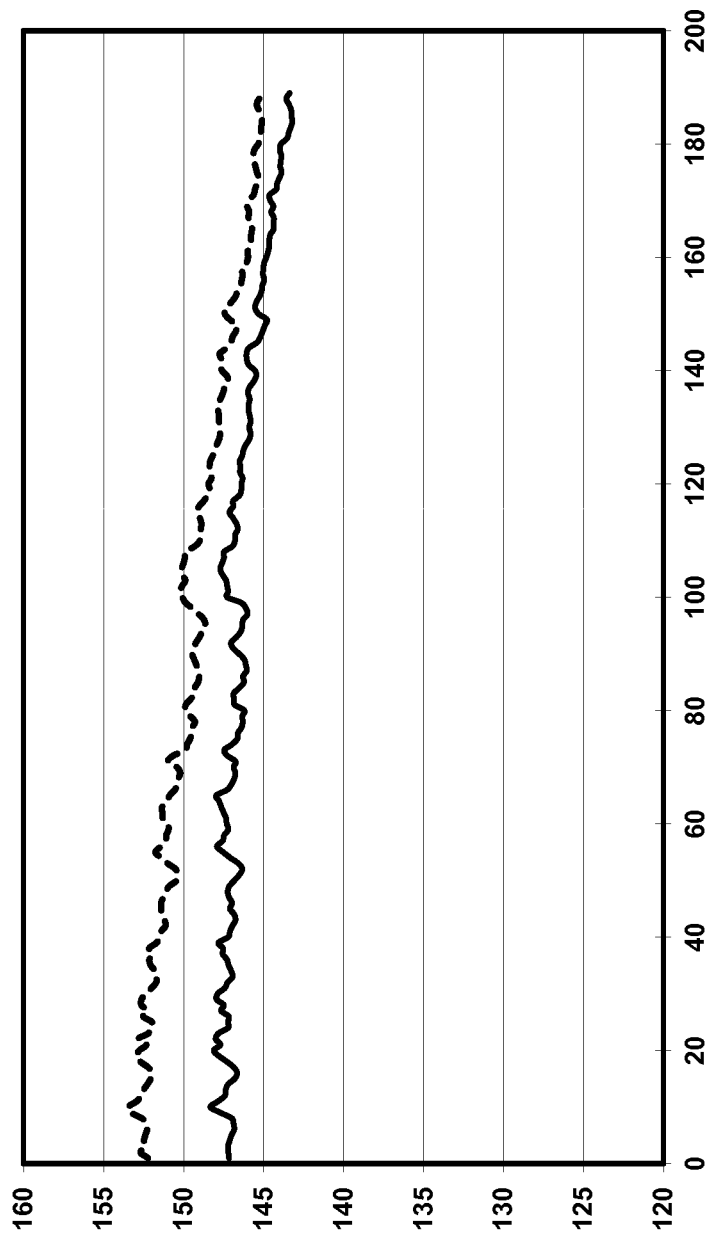

FLUORINATED CARBONATES COMPRISING TWO OXYGEN BEARING FUNCTIONAL GROUPS

This application is a U.S. national stage entry under 35 U.S.C. § 371 of International Application No. PCT/EP2015/067408 filed Jul. 29, 2015, which claims priority to European application No. 14178916.4 filed on Jul. 29, 2014. The entire content of these applications are explicably incorporated herein by this reference. The present invention concerns fluorinated carbonates comprising two oxygen bearing functional groups, methods for the preparation thereof, and their use as solvent or solvent additive for lithium ion batteries and supercapacitors.

This application claims priority to European application No. 14178916.4 filed 29$^{th}$ Jul. 2014, the whole content of this application being incorporated herein by reference for all purposes. The present invention concerns fluorinated carbonates comprising two oxygen bearing functional groups, methods for the preparation thereof, and their uses as solvent or solvent additive for lithium ion batteries and supercapacitors.

Lithium ion batteries, lithium air batteries and lithium sulfur batteries are well-known rechargeable means for storing electric energy. Lithium ion batteries comprise an electrolyte composition containing a solvent, a conductive salt and, often, additives. The solvent is an aprotic organic solvent which serves to dissolve the conductive salt. See, for example, WO 2007/042471 which provides information concerning suitable solvents. Suitable conductive salts are known in the art. $LiPF_6$ is a preferred conductive salt.

Capacitors are widely used devices for storing electrical energy. Among the various types of capacitors are electrochemical capacitors and electrolytic capacitors.

A hybrid supercapacitor is an electrochemical energy storage device that employs two different electrode types, the difference between the electrodes generally being in capacity or composition, and an electrolyte composition.

The optimization of the electrolyte compositions in hybrid supercapacitors still offers a significant potential to improve the performance properties of such systems.

Additives improve the properties of lithium ion batteries, e.g. by extending the cycle life. Fluoroalkyl alkyl carbonates, e.g. fluoromethyl methyl carbonate, and carbamates are known solvent additives for lithium ion batteries. WO 2011/006822 discloses the manufacture of 1-fluoroalkyl (fluoro)alkyl carbonates and carbamates. However, there is still a demand in the art for improved additives or solvents for lithium ion batteries.

Accordingly, the objective of the present invention is to provide improved additives for lithium ion batteries, lithium air batteries, lithium sulphur batteries or supercapacitors. The compounds of the present invention provide advantages like modifying the viscosity or reducing the flammability. Another advantage is the modification of the electrodes under formation of beneficial films or a solid electrolyte interphase (SEI). In this respect, the compounds of the present invention provide the advantage of two oxygen bearing functional groups and thus, a possible chelating effect, e.g. when in contact with the cathode material. Furthermore, the compounds of the invention advantageously lead to a better wettability of materials used in lithium ion batteries such as in particular a separator. The compounds of the invention can suitably assist in the protection against over-charging, for example, by serving as a redox shuttle. Yet another advantage is an increase in stability of the electrolyte composition, e.g. in presence of copper anions, which can be formed by possible degradation of certain current collector materials.

Furthermore, the compounds of the present invention advantageously show a high stability towards reduction while having a relatively low stability towards oxidation. Alternatively, the compounds of the present invention advantageously show a high stability towards oxidation while having a relatively low stability towards reduction. This property can lead to an increased performance of the battery, e.g. by modifying the electrodes of the battery, specifically by the formation on a protective layer on the electrode.

Additionally, the compounds of the present invention may increase energy density of a supercapacitor, their power density or their cycle life.

Accordingly, a first aspect of the present invention concerns a compound of the general formula (I), $R^1CFY-O-C(O)-O-[(CX^1X^2)_mO]_n-R^2$ (I), wherein $R^1$ is hydrogen, alkyl, alkylene, alkylyne, aryl, fluorosubstituted alkyl, or fluorosubstituted aryl; Y is hydrogen, fluorine, or alkyl; $R^2$ is hydrogen, alkyl, alkylene, alkylyne, aryl, fluorosubstituted alkyl, fluorosubstituted aryl, or $-C(O)-OR^{2'}$, wherein $R^{2'}$ is hydrogen, alkyl, aryl, fluorosubstituted alkyl, fluorosubstituted aryl; $X^1$ and $X^2$ are independently hydrogen, fluorine, or alkyl; and m and n are independently 1, 2, 3, 4, 5, 6, 7, 8, 9 or 10.

The term "fluorosubstituted alkyl" is intended to denote an alkyl group wherein at least one hydrogen atom is replaced by one fluorine atom.

The term "fluorosubstituted aryl" is intended to denote an aryl group wherein at least one hydrogen atom is replaced by one fluorine atom.

The term "aryl is intended to denote a monovalent radical derived from an aromatic nucleus such as, in particular, a C6-C10 aromatic nucleus, in particular phenyl or naphthyl. The aryl group can optionally be substituted, e.g. substituted with at least one alkyl group.

The term "alkyl group" is intended to denote an optionally substituted saturated monovalent hydrocarbon radical, such as, in particular, a C1-C6 alkyl. By way of example, mention may be made of methyl, ethyl, propyl, isopropyl, butyl, t-butyl, pentyl, isopentyl and hexyl. The alkyl may be optionally substituted, e.g. with halogen, aryl, or heteroaryl. A preferred alkyl group is methyl. The term "alkyl" also encompasses cycloalkyl groups. Cycloalkyl groups are optionally substituted cycles of saturated hydrocarbon-based groups. By way of example, mention may be made of cyclopropyl, cyclobutyl, cyclopentyl, and cyclohexyl.

The term "alkenyl" is intended to denote a straight or branched acyclic monovalent hydrocarbon radical having one or more carbon-carbon double bonds of either E or Z stereochemistry where applicable. The term includes, for example, vinyl, allyl, 1-butenyl, 2-butenyl, and 2-methyl-2-propenyl.

The term "alkynyl" is intended to denote a straight or branched chain monovalent hydrocarbon radical having from two to six carbon atoms and at least one carbon-carbon triple bond and optionally one or more carbon-carbon double bonds. Examples include ethynyl, propynyl and 3,4-pentadiene-1-ynyl.

In a preferred embodiment $R^1$ is hydrogen or alkyl, more preferably $R^1$ is ethyl.

In another preferred embodiment $R^2$ is alkyl, more preferably $R^2$ is methyl.

In another preferred embodiment $R^2$ is $-C(O)-OR^{2'}$, wherein $R^{2'}$ is hydrogen, alkyl, aryl, fluorosubstituted alkyl, fluorosubstituted aryl, more preferably $R^{2'}$ is fluorosubstituted alkyl, even more preferably $R^{2'}$ is —CHFCH$_3$.

In another preferred embodiment m is 2.

In another preferred embodiment n is 1.

The alkylene bridge between the two oxygen bearing groups is preferably an unsubstituted alkylene bridge, e.g. —CH$_2$—CH$_2$— or —CH$_2$—CH$_2$—CH$_2$—. Also preferably, the alkylene bridge is substituted with an alkyl group, more preferably with methyl, i.e. at least one of X and Y are alkyl, specifically methyl. Advantageously, the bridge has the structure —C(CH$_3$)H—CH$_2$—. In a specifically preferred embodiment n is 1, m is 2, X and Y are hydrogen and the bridge has the structure —CH$_2$—CH$_2$—.

In specific embodiments, the invention relates to a compound of one of the following structures:

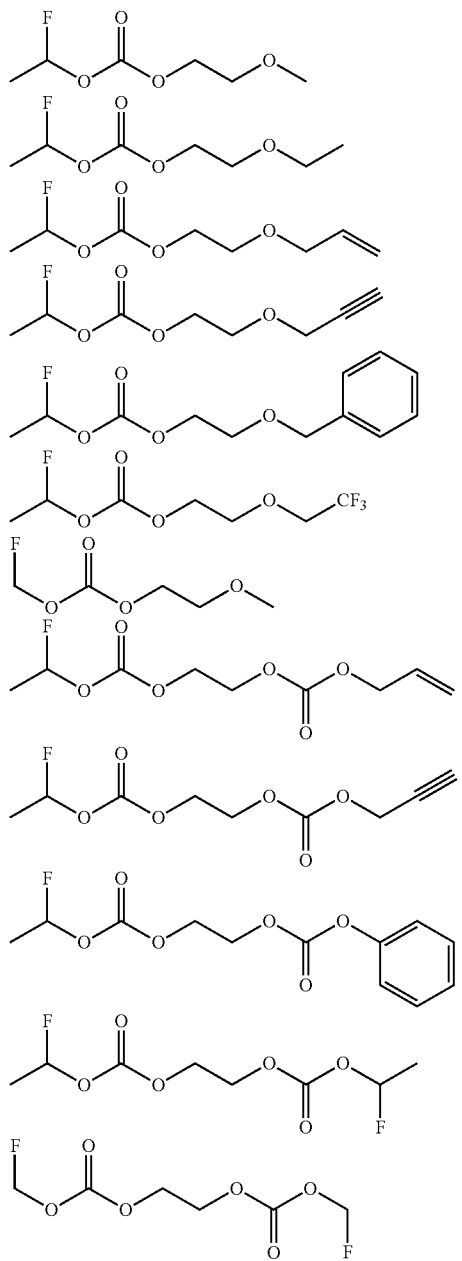

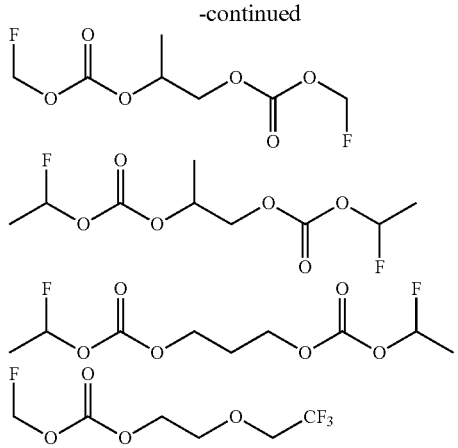

In a second aspect, the present invention concerns a method for the manufacture of a compound of the general formula (I), $R^1CFY$—O—C(O)—O—[(CX$^1$X$^2$)$_m$O]$_n$—R$^2$, wherein R$^1$ is hydrogen, alkyl, alkylene, alkylyne, aryl, fluorosubstituted alkyl, or fluorosubstituted aryl; Y is hydrogen, fluorine, or alkyl; R2 is hydrogen, alkyl, alkylene, alkylyne, aryl, fluorosubstituted alkyl, fluorosubstituted aryl, or —C(O)—OR$^{2'}$, wherein R$^{2'}$ is hydrogen, alkyl, aryl, fluorosubstituted alkyl, fluorosubstituted aryl; X$^1$ and X$^2$ are independently hydrogen, fluorine, or alkyl; and m and n are independently 1, 2, 3, 4, 5, 6, 7, 8, 9 or 10;

comprising a step of reacting a compound of general formula (II), $$R^1CFY\text{—}O\text{—}C(O)\text{—}F \qquad (II)$$

wherein R$^1$ and Y have the meaning is given above;
with an compound of general formula (III), $$HO\text{—}[(CX^1X^2)_mO]_n\text{—}OH \qquad (III)$$

wherein n, m, X$^1$, and X$^2$ have the meanings as given above.

Thus, according to this aspect of the invention, symmetrical compounds of general formula (I) can be prepared, i.e compounds bearing the same group on each side of the alkylene bridge.

Asymmetrical compounds of general formula (I) can be prepared by reacting a compound of formula (II) as described above with an alcohol of general formula (IV): HO—[(CX$^1$X$^2$)$_m$O]$_n$—R$^2$ (I), wherein R$^1$ is hydrogen, alkyl, alkylene, alkylyne, aryl, fluorosubstituted alkyl, or fluorosubstituted aryl; Y is hydrogen, fluorine, or alkyl; R$^2$ is hydrogen, alkyl, alkylene, alkylyne, aryl, fluorosubstituted alkyl, fluorosubstituted aryl, or —C(O)—OR$^{2'}$, wherein R$^{2'}$ is hydrogen, alkyl, aryl, fluorosubstituted alkyl, fluorosubstituted aryl; X$^1$ and X$^2$ are independently hydrogen, fluorine, or alkyl; and m and n are independently 1, 2, 3, 4, 5, 6, 7, 8, 9 or 10.

Compounds general formula (IV) wherein R$^2$ is —C(O)—OR$^{2'}$, wherein R$^{2'}$ is hydrogen, alkyl, aryl, fluorosubstituted alkyl, fluorosubstituted aryl, can advantageously be prepared by reacting a compound of general formula HO—[(CX$^1$X$^2$)$_m$O]$_n$—OH or HO—[(CX$^1$X$^2$)$_m$O]$_n$—O-PG, wherein PG is a hydroxyl-protecting group, with a compound of general structure Cl—C(O)—R$^{2'}$ or F—C(O)—OR$^{2'}$ and, in case of HO—[(CX$^1$X$^2$)$_m$O]$_n$—O-PG, subsequent removal of the hydroxyl-protecting group. Hydroxyl-protecting group are known to the skilled person. Examples of suitable hydroxyl-protecting groups include silyl ethers and esters, e.g. acetate.

Instead of the alcohol or diol, respectively, the corresponding alkali metal alkoxide can be applied, for example, the respective lithium, sodium, potassium or cesium alkoxide. The reaction can be performed in the presence of an HF scavenger e.g. LiF, NaF, KF or CsF, or in the presence of base, e.g. in the presence of ammonia or a primary, secondary or tertiary amine, e.g. triethylamine or pyridine. Preferably, it is performed in the absence of a base.

The molar ratio between is preferably chosen to be 0.9:1.1 hydroxyl groups per formiate molecules. The reaction temperature during the alcoholysis reaction is not critical. The reaction can be performed in any suitable reactor, e.g. in an autoclave. The reaction can be performed batch wise or continuously. The resulting reaction mixture can be separated by known methods, e.g. by distillation, precipitation and/or crystallization. If desired, the reaction mixture can be contacted with water to remove water-soluble constituents. Due to the specific type of reaction, organic carbonates with a higher degree of fluorination are formed, if at all, in only very minor proportions.

Compounds of general formula (II) can be prepared from the respective chloroalkyl chloroformates in a "Halex" type reaction, i.e. substitution of fluorine atoms for the chlorine atoms by fluorinating agents, as already described above, e.g. using a fluorinating reactant like alkali or alkaline earth metal fluorides, e.g. LiF, KF, CsF, NaF, $NH_4F$ or amine hydrofluorides, or the respective HF adducts. The chloroalkyl chloroformates themselves are available through the reaction between phosgene and an aldehyde as described in U.S. Pat. No. 5,712,407.

Alternatively, compounds of general formula (II) can be prepared from carbonyl fluoride and an aldehyde as described in WO 2011/006822. A process for the manufacture of fluoroformates and of the specific example $CH_3CHFC(O)F$ is described in WO 2011/006822.

Asymmetrical compounds of general formula (I) can be prepared by reacting a compound of formula (II) as described above with an alcohol of general formula (IV): $HO-[(CX^1X^2)_m O]_n-R^2$, wherein $R^1$ is hydrogen, alkyl, alkylene, alkylyne, aryl, fluorosubstituted alkyl, or fluorosubstituted aryl; Y is hydrogen, fluorine, or alkyl; $R^2$ is hydrogen, alkyl, alkylene, alkylyne, aryl, fluorosubstituted alkyl, fluorosubstituted aryl, or $-C(O)-OR^{2'}$, wherein $R^{2'}$ is hydrogen, alkyl, aryl, fluorosubstituted alkyl, fluorosubstituted aryl; $X^1$ and $X^2$ are independently hydrogen, fluorine, or alkyl; and m and n are independently 1, 2, 3, 4, 5, 6, 7, 8, 9 or 10.

In a third aspect, the present invention relates to the use of a compound of general formula (I) as described above as a solvent additive or as solvent for lithium ion batteries, lithium air batteries, lithium sulphur batteries, supercapacitors or hybrid supercapacitors.

In a fourth aspect, the present invention concerns a solvent composition for lithium ion batteries, lithium air batteries, lithium sulfur batteries, supercapacitors or hybrid supercapacitors, comprising at least one solvent useful for lithium ion batteries, further comprising at least one compound of general formula (I) as described above.

The compounds of general formula (I) are advantageously applied in solvent compositions or in electrolyte compositions together with at least one suitable solvent known to the expert in the field of lithium ion batteries or supercapacitors. For example, organic carbonates, but also lactones, formamides, pyrrolidinones, oxazolidinones, nitroalkanes, N,N-substituted urethanes, sulfolane, dialkyl sulfoxides, dialkyl sulfites, acetates, nitriles, acetamides, glycol ethers, dioxolanes, dialkyloxyethanes, trifluoroacetamides, are very suitable as solvents.

Preferably, the aprotic organic solvent is selected from the group of dialkyl carbonates (which are linear) and alkylene carbonates (which are cyclic), ketones, and formamides. Dimethyl carbonate, diethyl carbonate, methyl ethyl carbonate, cyclic alkylene carbonates, e.g. ethylene carbonate, propylene carbonate, and vinylidene carbonate, are examples of suitable solvents.

Fluorosubstituted compounds different from the compounds of general formula (I) as described above, for example, fluorosubstituted ethylene carbonates, polyfluorosubstituted dimethyl carbonates, fluorosubstituted ethyl methyl carbonates, and fluorosubstituted diethyl carbonates are other suitable solvents or suitable additional additives in the electrolytic compositions.

Other suitable additional additives useful in the electrolyte compositions according to the present invention are those described in WO2007/042471.

In a fifth aspect, present invention concerns an electrolyte composition for lithium ion batteries, lithium air batteries, lithium sulfur batteries, supercapacitors or hybrid supercapacitors, comprising at least one compound according to the invention, at least one solvent useful for lithium ion batteries or supercapacitors and at least one electrolyte salt.

The electrolyte composition, further to the at least one compound of general formula (I), comprises at least one dissolved electrolyte salt. Such salts have the general formula $M_aA_b$. M is a metal cation, and A is an anion. The overall charge of the salt $M_aA_b$ is 0. M is preferably selected from $Li^+$ and $NR_4^+$. Preferred anions are $PF_6-$, $PO_2F_2-$, $AsF_6-$, $BF_4-$, $ClO_4-$, $N(CF_3SO_2)_2-$, $N(FSO_2)_2-$ and $N(i-C_3F_7SO_2)_2-$.

Preferably, M is Li+ Especially preferably, M is $Li^+$ and the solution comprises at least one electrolyte salt selected from the group consisting of $LiBF_4$, $LiClO_4$, $LiAsF_6$, $LiPF_6$, $LiPO_2F_2$, $LiN(CF_3SO_2)_2$, $LiN(FSO_2)_2$ and $LiN(i-C_3F_7SO_2)_2$. Lithium bis(oxalato)borate can be applied as an additional additive. The concentration of the electrolyte salt is preferably between 0.8 and 1.2 molar, more preferably 1.0 molar. Often, the electrolyte composition may comprise $LiPF_6$ and $LiPO_2F_2$.

The compounds of formula (I) can be introduced into the electrolyte composition separately or in the form of a mixture with other compounds, e.g. as a mixture with one or more solvents used in the electrolyte composition or together with the electrolyte salt or together with other additives.

In a sixth aspect, the present invention relates to lithium ion batteries, lithium air batteries and lithium sulfur batteries comprising a solvent composition as outlined above or an electrolyte composition as outlined above.

The compounds according to this invention may advantageously be used as a solvent, a solvent additive or a co-solvent in a concentration from 1 to 15 wt %, preferably from 3 to 10 wt %, more preferably between 4 and 6 wt % and most preferably around 5 wt % relative to the total weight of the electrolyte composition.

Accordingly, another aspect of the invention concerns the use of a compound according to this invention in an electrolyte composition, in an electrolyte composition for Li ion batteries, Li air batteries or Li sulfur batteries, wherein the concentration of the compound according to any one of the claims 1 to 7 is from 1 to 15 wt %, preferably from 3 to 10 wt %, more preferably between 4 and 6 wt % and most preferably around 5 wt %; relative to the total weight of the electrolyte composition. Alternatively, the concentration is from 0.5 wt % to 1.5 wt %, specifically around 1 wt %.

Lithium ion batteries comprises an anode, preferably an anode made from carbon comprising a copper foil, a cathode, preferably a cathode made from lithium metal oxides comprising an aluminum foil, a separator, preferably a separator made from an insulating polymer, and a solvent composition or an electrolyte composition as described above. The foils used for anode and cathode are also called current collectors.

Should the disclosure of any patents, patent applications, and publications which are incorporated herein by reference conflict with the description of the present application to the extent that it may render a term unclear, the present description shall take precedence.

The invention will now be further described in examples without intending to limit it.

EXAMPLES

Example 1

Synthesis of ethane-1,2-diyl-bis(1-fluoroethyl) dicarbonate

A 2.5 l PFA-reactor equipped with a temperated double mantle, a reflux condenser and a mechanical stirrer was charged with 1315 g 1-fluoroethyl fluoroformate. After chilling the material to 3° C., a mixture of 267 g pyridine and 288 g ethylene glycol was slowly added over a period of 2.5 hours. The reaction temperature was kept below 55° C. After cooling down to room temperature, the mixture was washed three times with citric acid solution (30% in deionized water, 200 g, 100 g, 100 g). After drying over molecular sieve (120 g) for 3 days followed by filtration, the product was obtained as a colourless liquid in a yield of 1031 g with a purity >82% (GC assay). The product can optionally be purified further by distillation giving a purity >99.9% (GC assay).

Example 2

1-fluoroethyl 2-methoxyethyl carbonate

A 2.5 l PFA-reactor equipped with a temperated double mantle, a reflux condenser and a mechanical stirrer was charged with 1315 g 1-fluoroethyl fluoroformate. After chilling the material to 3° C., a mixture of 288 g pyridine and 800 g 2-methoxyethanol was slowly added over a period of 3 hours. The reaction temperature was kept below 45° C. After cooling down to room temperature, the mixture was washed three times with citric acid solution (30% in deionized water, 210 g, 130 g, 160 g). After drying over molecular sieve (140 g) for 3 days followed by filtration, the product was obtained as a colourless liquid in a yield of 1323 g (84%) with a purity >89% (GC assay). The product can optionally be purified further by distillation giving a purity >99.9% (GC assay).

Example 3

Linear Sweep Voltammetry (LSV)

Tests were performed in a beaker-type cell comprising three electrodes as follows for measurement of the oxidation potential:
a) Li metal as reference electrode
b) $LiCoO_2$ as working electrode
c) Li metal as counter electrode A standard electrolyte (1.0 M $LiPF_6$ in a 1:2 vol/vol % mixture of ethylene carbonate and dimethylcarbonate) was used. The respective inventive compound to be tested was added to this standard electrolyte at a concentration of 1 wt %.

Tests were performed using an electrochemical analyzer in a voltage range from 3.0 to 7.0 V with a scan rate of 0.1 $mVs^{-1}$.

FIG. 1 shows the results of the LSV testes.
Curve (1): standard electrolyte
Curve (2): standard electrolyte with 1 wt % ethane-1,2-diyl-bis(1-fluoroethyl) dicarbonate During the LSV test with the electrolyte comprising ethane-1,2-diyl-bis(1-fluoroethyl) dicarbonate, decomposition of the electrolyte was suppressed as compared to the standard STD electrolyte.

Example 4

Cyclic Voltammetry (CV)

Tests were performed in a beaker-type cell comprising three electrodes as follows :
d) Li metal as reference electrode
e) Artificial graphite (SCMG-AR) as working electrode
f) Li metal as counter electrode A standard electrolyte (1.0 M $LiPF_6$ in a 1:2 vol/vol % mixture of ethylene carbonate and dimethylcarbonate) was used. The respective inventive compound to be tested was added to this standard electrolyte at a concentration of 1 wt %.

Tests were performed for 3 cycles using an electrochemical analyzer in a voltage range from 3.0 to 0.0 V with a scan rate of 1.0 $mVs^{-1}$.

FIG. 2 shows the results (3 time cycles) of the CV test.
Curve (1): standard electrolyte with 1 wt % ethane-1,2-diyl-bis(1-fluoroethyl) dicarbonate During the first cycle of the CV test, SEI formation (reduction) on the surface of the anode starting at 0.9V was shown. The electrolyte decomposition was therefore prevented in the second and third cycle.

Example 5

Performance Testing—Mono Full Cell

Test system: Mono full cell consisting of: [$LiNi_{1/3}Co_{1/3}Mn_{1/3}O_2$ (Ecopro): Super-P® (conductive carbon black obtainable from MMM Carbon, Belgium): PVdF (Solef® 5130 from Solvay Specialty Polymers) binder=92:4:4 (wt. %)] as positive electrode and [SCMG-AR® (artificial graphite obtainable from Showa Denko): Super-P® (conductive carbon black obtainable from MMM Carbon, Belgium): PVdF (Solef® 5130 from Solvay Specialty Polymers) binder=90:4:6 (wt. %)] as negative electrode. Polyethylene was used as separator. A standard electrolyte composition [(1.0M $LiPF_6$/ethylene carbonate+dimethyl carbonate (1:2 (v/v)] was used to which the fluorinated additives according to the invention were added under dry room atmosphere.

The preparation of the mono full cells consisted of the following steps in that order: (1) mixing, (2) coating & drying, (3) pressing, (4) slitting, (5) tap welding, (6) pouch cutting, (7) assembly (stacking),(8) mono cell 2-side sealing, (9) electrolyte filling, and (10) vacuum sealing.

For the Cycle Performance, 200 cycles were performed in the range of 3.0V~4.4V under C-rate of 1.0.

FIG. 3 shows the unexpected advantageous effect of ethan-1,2-diyl-bis(1-fluoroethyl dicarbonate) in a concentration of 1 wt % (x-axis: cycle number, y-axis: discharge capacity [mAh/g]): initial discharge capacity was 152.2 (mAh/g) and after 200 discharge cycles, capacity was 144.3 (mAh/g). In a comparative example, use of the standard electrolyte composition resulted in an initial discharge capacity of 147.2 (mAh/g), and after 200 cycles, discharge capacity of 143.2 (mAh/g).

The invention claimed is:

1. A method for the manufacture of a compound of general formula (I),

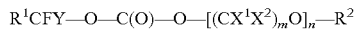

wherein $R^1$ is hydrogen, alkyl, alkylene, alkylyne, aryl, fluorosubstituted alkyl, or fluorosubstituted aryl ; Y is hydrogen, fluorine, or alkyl; $R^2$ is hydrogen, alkyl, alkylene, alkylyne, aryl, fluorosubstituted alkyl, fluorosubstituted aryl, or —C(O)—$OR^{2'}$, wherein $R^{2'}$ is hydrogen, alkyl, aryl, fluorosubstituted alkyl, fluorosubstituted aryl; $X^1$ and $X^2$ are independently hydrogen, fluorine, or alkyl; and m and n are independently 1, 2, 3, 4, 5, 6, 7, 8, 9 or 10;

the method comprising a step of reacting a compound of general formula (II), $$R^1CFY\text{—}O\text{—}C(O)\text{—}F \qquad (II)$$

wherein $R^1$ and Y have the meaning is given above;
with an compound of general formula (III), $$HO\text{—}[(CX^1X^2)_mO]_n\text{—}OH \qquad (III)$$

wherein n, m, $X^1$, and $X^2$ have the meanings as given above.

2. A solvent additive or solvent for lithium ion batteries, lithium air batteries, lithium sulphur batteries, supercapacitors or hybrid supercapacitors comprising a compound of general formula (I),

wherein $R^1$ is hydrogen, alkyl, alkylene, alkylyne, aryl, fluorosubstituted alkyl, or fluorosubstituted aryl;
Y is hydrogen, fluorine, or alkyl;
$R^2$ is hydrogen, alkyl, alkylene, alkylyne, aryl, fluorosubstituted alkyl, fluorosubstituted aryl, or —C(O)—$OR^{2'}$, wherein $R^{2'}$ is hydrogen, alkyl, aryl, fluorosubstituted alkyl, fluorosubstituted aryl; $X^1$ and $X^2$ are independently hydrogen, fluorine, or alkyl; and m and n are independently 1, 2, 3, 4, 5, 6, 7, 8, 9 or 10.

3. A solvent composition for lithium ion batteries, lithium air batteries, lithium sulfur batteries, supercapacitors or hybrid supercapacitors, comprising at least one solvent useful for lithium ion batteries or supercapacitors and at least one compound of general formula (I),

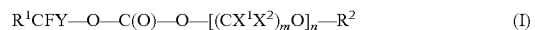

wherein $R^1$ is hydrogen, alkyl, alkylene, alkylyne, aryl, fluorosubstituted alkyl, or fluorosubstituted aryl;
Y is hydrogen, fluorine, or alkyl;
$R^2$ is hydrogen, alkyl, alkylene, alkylyne, aryl, fluorosubstituted alkyl, fluorosubstituted aryl, or —C(O)—$OR^{2'}$, wherein $R^{2'}$ is hydrogen, alkyl, aryl, fluorosubstituted alkyl, fluorosubstituted aryl; $X^1$ and $X^2$ are independently hydrogen, fluorine, or alkyl; and m and n are independently 1, 2, 3, 4, 5, 6, 7, 8, 9 or 10.

4. An electrolyte composition for lithium ion batteries, lithium air batteries, lithium sulfur batteries, supercapacitors or hybrid supercapacitors, comprising at least one solvent useful for lithium ion batteries or supercapacitors, at least one electrolyte salt, and at least one compound of general formula (I),

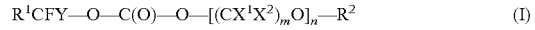

wherein $R^1$ is hydrogen, alkyl, alkylene, alkylyne, aryl, fluorosubstituted alkyl, or fluorosubstituted aryl;
Y is hydrogen, fluorine, or alkyl;
$R^2$ is hydrogen, alkyl, alkylene, alkylyne, aryl, fluorosubstituted alkyl, fluorosubstituted aryl, or —C(O)—$OR^{2'}$, wherein $R^{2'}$ is hydrogen, alkyl, aryl, fluorosubstituted alkyl, fluorosubstituted aryl; $X^1$ and $X^2$ are independently hydrogen, fluorine, or alkyl; and m and n are independently 1, 2, 3, 4, 5, 6, 7, 8, 9 or 10.

5. A lithium ion battery, a lithium air battery, a lithium sulfur battery, a supercapacitor or a hybrid supercapacitor containing at least one compound of general formula (I),

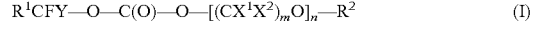

wherein $R^1$ is hydrogen, alkyl, alkylene, alkylyne, aryl, fluorosubstituted alkyl, or fluorosubstituted aryl;
Y is hydrogen, fluorine, or alkyl;
$R^2$ is hydrogen, alkyl, alkylene, alkylyne, aryl, fluorosubstituted alkyl, fluorosubstituted aryl, or —C(O)—$OR^{2'}$, wherein $R^{2'}$ is hydrogen, alkyl, aryl, fluorosubstituted alkyl, fluorosubstituted aryl; $X^1$ and $X^2$ are independently hydrogen, fluorine, or alkyl; and m and n are independently 1, 2, 3, 4, 5, 6, 7, 8, 9 or 10.

* * * * *